(12) United States Patent
Mylari

(10) Patent No.: US 8,853,259 B2
(45) Date of Patent: Oct. 7, 2014

(54) METFORMIN DERIVATIVES FOR TREATING DIABETES AND DIABETES COMPLICATIONS

(71) Applicant: Banavara L. Mylari, Lutz, FL (US)

(72) Inventor: Banavara L. Mylari, Lutz, FL (US)

( * ) Notice: Subject to any disclaimer, the term of this patent is extended or adjusted under 35 U.S.C. 154(b) by 0 days.

(21) Appl. No.: 14/174,454

(22) Filed: Feb. 6, 2014

(65) Prior Publication Data

US 2014/0221467 A1     Aug. 7, 2014

Related U.S. Application Data

(60) Provisional application No. 61/761,768, filed on Feb. 7, 2013.

(51) Int. Cl.
    *A61K 31/385*     (2006.01)
    *C07D 339/04*     (2006.01)

(52) U.S. Cl.
    CPC .................................. *A61K 31/385* (2013.01)
    USPC ............................................. 514/440; 549/39

(58) Field of Classification Search
    CPC ........................... A61K 31/385; C07D 339/04
    USPC ............................................. 514/440; 549/39
    See application file for complete search history.

(56) References Cited

U.S. PATENT DOCUMENTS 8,765,811 B2 *    7/2014    Mylari et al. .................. 514/555

* cited by examiner

*Primary Examiner* — Taofiq A Solola
(74) *Attorney, Agent, or Firm* — Robert D. Katz, Esq.; Eaton & Van Winkle LLP

(57) ABSTRACT

The invention provides mutual ternary salts of metformin, lipoic acid and acidic amino acids such as aspartic acid and glutamic acid. The invention further provides treatment of prediabetes, diabetes, diabetic complications and/or other conditions in mammals in a method that comprises administering an effective amount of one or more of the foregoing compositions to a mammal in need of such treatment.

26 Claims, No Drawings

METFORMIN DERIVATIVES FOR TREATING DIABETES AND DIABETES COMPLICATIONS

CROSS-REFERENCE TO RELATED APPLICATION

This application claims priority based on U.S. Provisional Application Ser. No. 61/761,768, filed Feb. 7, 2013, the entire contents of which are incorporated by reference.

FIELD OF THE INVENTION

The present invention relates to mutual salts of metformin, lipoic acid and aspartic acid or glutamic acid.

BACKGROUND OF THE INVENTION

Diabetes mellitus has become pandemic and according to a forecast by the World Health Organization, there will be a sharp increase in the number of diabetic patients by the year 2030. This is an ominous forecast, because managing the long-term complications of diabetes, which include nephropathy, neuropathy, retinopathy, and cardiovascular complications, will have a serious impact on public health budgets. The hallmark of diabetes is chronically elevated blood glucose levels. It is also known that abnormally elevated glucose levels have an adverse impact on glutathione levels in key diabetic tissues. Furthermore, increased oxidative stress and increased production of reactive oxygen species are implicated under hyperglycemic conditions.

In spite of the early discovery of insulin and its subsequent widespread use in the treatment of diabetes, and the later discovery of and use of sulfonylureas, and thiazolidenediones, such as troglitazone, rosiglitazone or pioglitazone, as oral hypoglycemic agents, the treatment of diabetes remains less than satisfactory.

The use of insulin requires multiple daily doses, usually by self-injection. Determination of the proper dosage of insulin requires frequent estimations of the sugar in urine or blood. Treatment of non-insulin dependent diabetes mellitus (type 2) diabetes (NIDDM) usually involves a combination of diet, exercise, oral hypoglycemic agents, e.g., thiazolidenediones, and, in more severe cases, insulin. However, the clinically available hypoglycemic agents can either have side effects limiting their use, or may not be effective with a particular patient. In the case of insulin dependent diabetes mellitus (Type 1), insulin administration usually constitutes the primary course of therapy.

The biguanide metformin is a known compound approved by the U.S. Food & Drug Administration for the therapeutic treatment of diabetes. The compound and its preparation and use are disclosed, for example, in U.S. Pat. No. 3,174,901. Metformin is orally effective in the treatment of type 2 diabetes. Metformin (N,N-dimethylimidodicarbonimidic diamide) is a biguanide, anti-hyperglycemic agent currently marketed in the United States in the form of its hydrochloride salt, 1,1-dimethylbiguanide hydrochloride (Formula I):

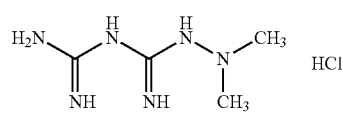

Formula I

Metformin hydrochloride can be purchased commercially and can also be prepared, for example, as disclosed in *J. Chem. Soc.*, (1922), 121, 1790.

U.S. Pat. No. 7,973,073 B2 (Mylari) describes a method for treating diabetes or diabetic complications using metformin R-(+) lipoate.

According to United Kingdom Perspective Diabetes Study (UKPDS) (Clarke et al. *Diabetologa*, (2005), 48, 868-877), metformin therapy was cost-saving and increased quality-adjusted life expectancy. In the UKPDS, overweight and obese patients randomized to initial therapy with metformin experienced significant reductions in myocardial infarction and diabetes-related deaths. Metformin does not promote weight gain and has beneficial effects on several cardiovascular risk factors. Accordingly, metformin is widely regarded as the drug of choice for most patients with Type 2 diabetes.

Alpha-lipoic acid, commonly known as lipoic acid, has a variety of names, including thioctic acid, 1,2-dithiolane-3-pentanoic acid, 1,2-ditholane-3-valeric acid, 6,8-thioctic acid5-[3Cl,2-dithiolanyl)]-pentanoic acid, delta-[3-(1,2dithiacyclopentyl)]pentanoic acid and pyruvate oxidation factor. Alpha lipoic acid has an asymmetric center and is usually employed in the form of a racemic mixture of its R- and S-enantiomers, particularly in nutritional supplements. All published clinical trials have thus far been conducted with racemic alpha-lipoic acid.

Alpha-lipoic acid (herein referred to as lipoic acid) is an antioxidant and is a scavenger of reactive oxygen species (ROS). It chelates metals and recycles endogenous antioxidants. Lipoic acid can scavenge singlet oxygen, $H_2O_2$, hydroxyl radical, NO, and $ONOO^-$. The reduced form of lipoic acid, dihydrolipoic acid, can further scavenge $O_2^-$, and peroxy radicals. Lipoic acid can also chelate several divalent cations, e.g., $Mn^{2+}$, $Cu^{2+}$, $Zn^{2+}$, $Cd^{2+}$, and $Pb^{2+}$. Therefore, lipoic acid can inhibit ascorbate-induced production of $H_2O_2$ by $Cu^{2+}$. Lipoic acid can recycle endogenous antioxidants, such as glutathione (GSH), and vitamin C. GSH protects tissues from oxidative stress. Lipoic acid can also circulate plasma levels of lactate and pyruvate in diabetic patients. Estrada et al., (*Diabetes*. 1996, 45, 1798-1804) report that lipoic acid induces GLUTs (glucose transporters) and glucose uptake and this suggests that lipoic acid may also stimulate the insulin signaling pathway. Lipoic acid administration has been shown to be active in oxidative stress models including in ischemia-reperfusion injury model. Furthermore, lipoic acid can function as a redox regulator of thioredoxin and NF-kappa B transcription factor. Many of the aspects of lipoic acid described herein are included in the review by Smith et al., *Current Medicinal Chemistry* (2004), 11, 1135-1146.

While lipoic acid is practically insoluble in water (Merck Index, 11th ed. at 9259), the salts of the present invention are markedly more water soluble to provide concomitant delivery of both metformin and lipoic acid, thus providing a dual action in targeting both blood glucose control and long-term diabetes complications, such as nephropathy, neuropathy, retinopathy, cataracts and cardiovascular complications. Furthermore, the new salts would offer a patient friendly dosage form of two active therapies in a fixed dosage combination with increased reliability for daily patient compliance.

Prediabetes is a syndrome. Many patients with type 2 diabetes and with a prediabetic condition known as metabolic syndrome suffer from a variety of lipid disorders including elevated triglycerides. The body uses triglycerides to store fat, but high (>200 mg/dl) and very high (>500 mg/dl) triglycerides are associated with atherosclerosis which increases the patients' risk of heart attack and stroke.

Incipient diabetes with impaired glucose tolerance is another prediabetic condition. Overall, type 2 diabetes and incipient diabetes with impaired glucose tolerance are intimately intertwined with obesity, hyperlipidemia, including hypertriglyceridemia, and cardiovascular complications including arrhythmia, cardiomyopathy, myocardial infarction, stroke and heart failure. Clinically, pre-diabetes means that blood sugar level is higher than normal, but it's not yet increased enough to be classified as type 2 diabetes. Still, without intervention, prediabetes is likely to become type 2 diabetes over time.

Diabetic complications include cataracts, nephropathy, neuropathy, retinopathy, and cardiovascular complications, including myocardial ischemia, cardiomyopathy, and heart failure.

Also, diabetic patients have impaired circulation that manifests itself in peripheral vascular disease (PVD) and the slow healing of wounds in the foot and lower leg and puts the patient at risk for amputation.

Each of the citations herein, whether patents or publications, is incorporated by reference.

SUMMARY OF THE INVENTION

The present invention provides compositions of having the following structure:

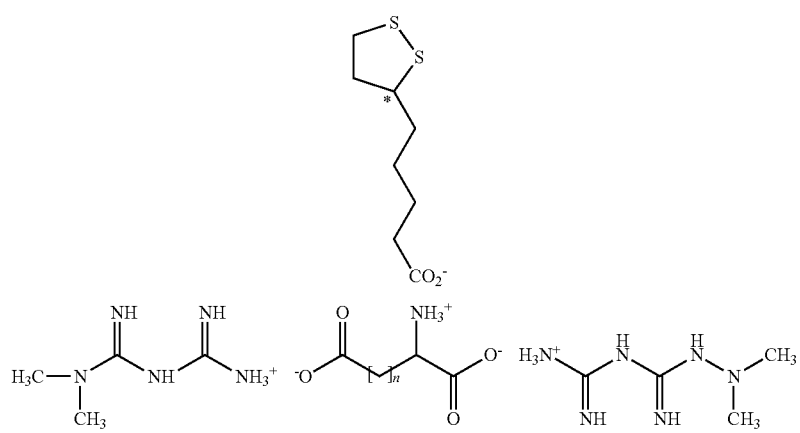

Formula II

Wherein n is 1 to 6 and the chirality at the *carbon atom is (RS,±)), R (+) or S (−).

It should be understood that the location of the positive charge in metformin is illustrative only and it could be located on other nitrogen atoms in metformin.

The compositions are typically compounds in the form of mutual salts of metformin, lipoic acid, including RS (racemic), R and S enantiomers and aspartic acid or glutamic acid in which the metformin moiety is protonated and the acid moieties are at least partially in ionic form. In some instances, however, for example depending on the pH of the environment, the composition may be in the form of a mixture of the metformin and acid components. The invention also provides pharmaceutical compositions comprising compositions of formula II and pharmaceutically acceptable excipients. The invention further provides methods for treating diabetes (especially type 2 diabetes), prediabetes, obesity, diabetic complications such as nephropathy, neuropathy, retinopathy, cataracts and cardiovascular complications such as myocardial infarction and cardiomyopathy. The compounds and compositions of this invention may provide high blood levels of the compositions of formula II, when administered to patients, preferably by oral administration.

Particularly useful compounds are those wherein n is 1 and 2.

DETAILED DESCRIPTION OF THE PREFERRED EMBODIMENTS

Compounds of the present invention can be considered as designer dual-acting drugs and additionally possess a means for improving the bioavailability of their component moieties as a result of their high degree of water solubility.

The present invention provides a pharmaceutical composition of the invention comprising compound of formula II and a pharmaceutically-acceptable carrier, vehicle or diluent.

The pharmaceutical composition may, for example, be in a form suitable for oral administration as a tablet, capsule, pill, powder, sustained release formulation, solution, suspension, for parenteral injection as a sterile solution, suspension or emulsion. Such compositions and methods for their preparation may be found, for example, in *Remington's Pharmaceutical Sciences*. 19th ed. (Mack 1995). The pharmaceutical composition may be in unit dosage forms suitable for single administration of precise dosages. The pharmaceutical composition will include a conventional pharmaceutical carrier or excipient and an active compound.

Formulations suitable for oral administration Include solid formulations such as tablets, capsules containing particulates, liquids, or powders, lozenges (including liquid-filled lozenges), chews, multi- and nano-particulates, gels, solid solution, liposome, films, ovules, sprays and liquid formulations.

Tablet dosage forms typically also include a disintegrant (such as sodium starch glycolate, sodium carboxymethyl cellulose, calcium carboxymethyl cellulose, polyvinylpyrrolidone, methyl cellulose, microcrystalline cellulose, lower alkyl-substituted hydroxypropyl cellulose, starch, pregelatinized starch and sodium alginate), a binder (such as microcrystalline cellulose, gelatin, a sugar, polyethylene glycol, natural and synthetic gums, polyvinylpyrrolidone, pregelatinized starch, hydroxypropyl cellulose and hydroxypropyl methylcellulose), and a lubricant (such as magnesium stearate, calcium stearate, zinc stearate, sodium stearyl fumarate, and mixtures of magnesium stearate with sodium lauryl sulfate). A diluent such as lactose, mannitol, xylitol, dextrose, sucrose, sorbitol, microcrystalline cellulose, starch and dibasic calcium phosphate dehydrate) may also be present. Compositions of the invention may also be administered for example as capsules made, for example, from gelatin or hydroxypropylmethylcellulose.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil. Liquid formulations may also be prepared by the reconstitution of a solid, for example, from a sachet. The compositions of the invention may also be used in fast-dissolving, fast-disintegrating dosage forms such as those described in *Expert Opinion in Therapeutic Patents.* 11 (6), 981-986, by Liang and Chen (2001).

The term alpha-lipoic acid includes racemic (RS) compound, and R, and S enantiomeric compounds.

The terms "treating", "treat", or "treatment" as used herein include curative, preventive (e.g., prophylactic) and palliative treatment.

Other formulations will be apparent to those skilled in the art.

The invention further provides methods for treatment or lowering the risk of developing conditions such as diabetes, especially type 2 diabetes, prediabetes, obesity, myocardial infarction and cardiomyopathy by administering therapeutically effective amounts of compositions of Formula II. Such compositions may also be used to treat or prevent the progression of diabetic complications such as nephropathy, neuropathy, retinopathy, cataracts and cardiovascular complications such as myocardial ischemia, and cardiomyopathy. Suitable dosages may be determined by conventional means.

The following examples are meant to be illustrative but not limited of the scope of the invention.

EXAMPLE I

Diabetic Rat Model

The following example describes a diabetic rat model that may be used for determination of conditions leading to a method for treatment and prevention of post-ischemic damage of the heart and heart tissue.

Spontaneously diabetic Bio-Bred (BB/W) rats from the colony maintained at the University of Massachusetts Medical Center, Worcester, Mass. were used in this study. BB/W rats were chosen for the current study because the BB/W rats have been considered a useful model of autoimmune human insulin-dependent diabetes mellitus (IDDM). Like human IDDM, spontaneous diabetes appears during adolescence, with an abrupt clinical onset characterized by weight loss, hyperglycemia, hypoinsulinemia, and ketonuria. As in the case of human diabetics, pathological changes in retina, myocardium, liver, kidney, bone metabolism and peripheral nerves have all been well documented in BB rats, as described in *Diab. Metab. Rev.,* 8:9 (1992). The BB/W rats were 3 to 4 months old and weighed about 300 to 350 g. The BB/W rats received daily insulin, which was discontinued 24 h prior to performing the isolated heart perfusion studies, leading to a hyperglycemic state. The rats were acutely diabetic, receiving 2.02±0.04 units of insulin daily, and had been diabetic for at least 12±3 days. The mean blood glucose levels in these diabetic rats were 386±24 mg/dL. The age-matched non-diabetic controls had mean blood glucose levels of 92±12 mg/dL.

EXAMPLE II

Isolated Perfused Heart Model

This example describes an isolated perfused rat heart model used in development of the invention. Studies are performed using an isovolumic isolated rat heart preparation. Acutely diabetic male BB/W rats and non-diabetic age-matched (3 to 4 months old) control are pretreated with heparin (1000 u; IP), followed by sodium pentobarbital (65 mg/kg; IP). After deep anesthesia is achieved, as determined by the absence of a foot reflex, the hearts are rapidly excised and placed into iced saline. The arrested hearts are retrograde perfused in a non-recirculating model through the aorta within 2 minutes following their excision. Left ventricular developed pressure (LVDP) is determined using a latex balloon in the left ventricle with high pressure tubing connected to a pressure transducer. Perfusion pressure is monitored using high pressure tubing off the perfusion line. Hemodynamic measurements are recorded on a 4-channel Gould recorder. The system has two parallel perfusion lines with separate oxygenators, pumps and bubble traps, but common temperature control allows rapid change perfusion media. The hearts are perfused using an accurate roller pump. The perfusate consists of 118 mM NaCl, 0.47 mM KCl, 12 mM $CaCl_2$, 12 mM MgCl2, 25 mM $NaHCO_3$, and the substrate 11 mM glucose. The perfusion apparatus is tightly temperature-controlled, with heated baths being used for the perfusate and for the water jacketing around the perfusion tubing to maintain heart temperature at 37±0.5° C. under all conditions. The oxygenated perfusate in the room temperature reservoir is passed through 25 ft. of thin-walled silicone tubing surrounded by distilled water at 37° C. saturated with 95% oxygen.

The perfusate then enters the water-jacketed (37° C.) tubing leading to the heart through a water jacketed bubble trap. This preparation provides excellent oxygenation that routinely has been stable for 3 to 4 hours.

EXAMPLE III

Model for Zero-/Low Ischemia

This example describes a procedure used for study of zero-flow ischemia in diabetic control, diabetic treated, non-diabetic treated and control isolated hearts. Diabetic control (DC), diabetic treated (DZ), normal (C) control, and normal treated (CZ) hearts are subjected to 20 minutes of normoxic perfusion followed by 20 minutes of zero-flow ischemia where the perfusate flow is completely shut off, followed by 60 minutes of reperfusion. Hearts are treated with 10 μM compounds of the formula II, wherein n is 1 or 2 and the chirality at the *carbon atom is (RS,±)), R (+) or S (−). In the present examples compounds of the Formula II treated diabetic group (DZ), hearts are subjected to 10 minutes of normoxic perfusion with normal Krebs-Henseleit buffer and 10 minutes of normoxic perfusion with Krebs-Henseleit buffer containing 10 μM present compounds of Formula II. The hearts are then subjected to 20 minutes of zero-flow ischemia followed by 60 minutes of reperfusion. In order to avoid any variability in reperfusion conditions, both DC and DZ hearts are reperfused with normal Krebs-Henseleit buffer.

EXAMPLE IV

Model for Low-flow Ischemia

This example describes a procedure used for study of low-flow ischemia in diabetic controls, diabetic treated, non-diabetic treated and non-diabetic control isolated hearts. Diabetic control hearts (DC) are subjected to 20 minutes of normoxic perfusion at a flow rate of 12.5 mL/minute followed by 30 minutes of low-flow ischemia where the perfusate flow is slowed down to 1.25 mL/min, that is about 10% of normal perfusion, followed by 30 minutes of reperfusion at a normal flow rate (12.5 mL/min). In the compounds of the Formula II, wherein n is 1 or 2 and the chirality at the *carbon atom is (RS,±)), R (+) or S (−) treated diabetic or non-diabetic groups (DZ or CZ), hearts are subjected to 10 minutes of normoxic perfusion (flow rate 12.5 mL/min) with normal Krebs-Henseleit buffer and 10 minutes of normoxic perfusion with Krebs-Henseleit buffer containing 10 µM present compounds metformin the formula II. The hearts are subjected to 30 minutes of low-flow ischemia (flow rate 1.25 mL/min) and 30 minutes of reperfusion at normal flow rate (12.5 mL/min).

Animal models to determine the effects of compounds of the invention on diabetes and complications of diabetes have been reviewed by Tirabassi et al., *ILAR Journal*, 2004, 45, 292-302. Antidiabetic activity may also be tested according to protocols described in the following patents: U.S. Pat. Nos. 4,340,605; 4,342,771; 4,367,234; 4,617,312; 4,687,777 and 4,703,052. Additional references relevant to this application include the following: French Patent 2796551 and United States Published Patent Application No. 2003/0220301.

EXAMPLE V

Synthesis of Compounds

One equivalent of aspartic acid or glutamic acid may be dissolved in an appropriate reaction inert solvent. The solvent may be a polar solvent such as water. As used herein, the expression "reaction inert solvent" refers to a solvent or a mixture of solvents which does't interact with starting materials, reagents, intermediates or products in a manner which adversely affects the yield of the desired product. Preferred solvents include methanol, ethanol, n-propanol, isopropanol, acetone, acetonitrile ethyl methyl ketone, diethyl ketone and methyl isobutyl ketone. Particularly preferred solvents for this reaction are is acetone, acetonitrile and methanol. To this solution may be added a solution of one equivalent of lipoic acid (Both racemic lipoic acid and its enantiomers (R and S) are commercially available.) and the reaction mixture can be stirred at about ambient temperature to about the reflux temperature of the solvent being used for about ½ hour to about six hours, preferably at ambient temperature for about two hours. To this reaction mixture a solution of metformin free base, prepared according the method of U.S. Pat. No. 3,957,853 (hereby incorporated herein by reference) may be added. The reaction mixture can be stirred at about ambient temperature to about the reflux temperature of the solvent being used for about two hours to about six hours, preferably at ambient temperature for about two hours. The metformin salts of this invention, as shown in Formula II, can be isolated from the reaction mixture by methods well known to those skilled in the art, including according to the method of U.S. Pat. No. 3,957,853. The methods preparation metformin salts of the present invention can include the other possible sequential addition of aspartic acid, glutamic acid, and lipoic acid and metformin base.

EXAMPLE VI

Preparation of metformin-L-glutamic acid-R (+) lipoic acid salt

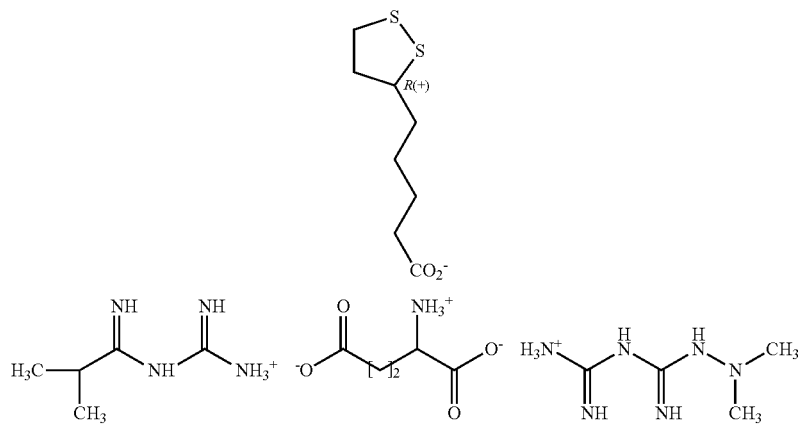

Metformin hydrochloride (N,N-dimethylimidodicarbonimidic diamide hydrochloride, 5.25 g, 0.032 mol) was stirred in 1N sodium hydroxide (32 mL, 0.032 mol) at room temperature for 30 min. Water was removed from the mixture under vacuo. The crude mixture was treated with ethanol (100 mL) and stirred for 10 min. The white residue was filtered off and ethanol was removed under vacuum to get a white residue. The ethanol treatment was repeated again to get a white solid (quantitative), which was dried in pump and used as metformin free base.

Method 1: Metformin free base (1.29 g, 0.010 mol) was taken in methanol (15 mL) and while stirring L-Glutamic acid (0.74 g, 0.050 mol) was added as solid. Lipoic acid (1.03 g, 0.050 mol) was separately dissolved in methanol (15 mL) and added to this mixture through a in-line syringe filter (to remove polymeric material, if any). The mixture was continued to stir for 30 min. Leaving the mixture in the refrigerator did not cause any precipitation of the salt, hence the solvent was removed under vacuo and dried in high vacuum pump. Metformin.L-Glutamic acid.R-Lipoic acid salt (2.9 g) was obtained as light yellow foamy solid. This solid is high hygroscopic and turns into gummy residue on exposure to air. The residue was suspended in acetonitrile (30 mL) and stirred for 18 h. Filtered the pale yellow solid and dried in vacuum for 16 h to get 2.32 g of 3. $^1$H NMR (200 MHz, $D_2O$) δ 1.15-2.1 (10H, m), δ 2.1-2.42 (5H, m), δ2.88 (12H, s), δ 2.95-3.12 (1H, m) δ 3.48-3.62 (2H, m); $^{13}$C NMR (200 MHz, $D_2O$) $δ_c$ 25.86, 27.25, 28.68, 33.81, 34.14, 37.66, 38.34, 40.51, 54.95, 56.93, 158.63, 160.28, 174.80, 181.44, 183.81.

Method 2: Lipoic acid (1.03 g, 0.050 mol) was dissolved in acetonitrile (30 mL) and to this Metformin free base (1.29 g, 0.010 mol) and L-Glutamic acid (0.74 g, 0.050 mol) were added as solid. The resulting mixture was stirred for 2 h and filtered. The pale yellow solid was dried in vacuo for 16 h to get 2.56 g of 3. $^1$H NMR (200 MHz, D$_2$O) δ 1.15-2.1 (10H, m), δ 2.1-2.42 (5H, m), δ 2.88 (12H, s), δ 2.95-3.12 (1H, m) δ 3.48-3.62 (2H, m); $^{13}$C NMR (200 MHz, D$_2$O) δ$_c$ 25.86, 27.25, 28.68, 33.81, 34.14, 37.66, 38.34, 40.51, 54.95, 56.93, 158.63, 160.28, 174.80, 181.44, 183.81.

What is claimed is:

1. A compound having the following structure (Formula II):

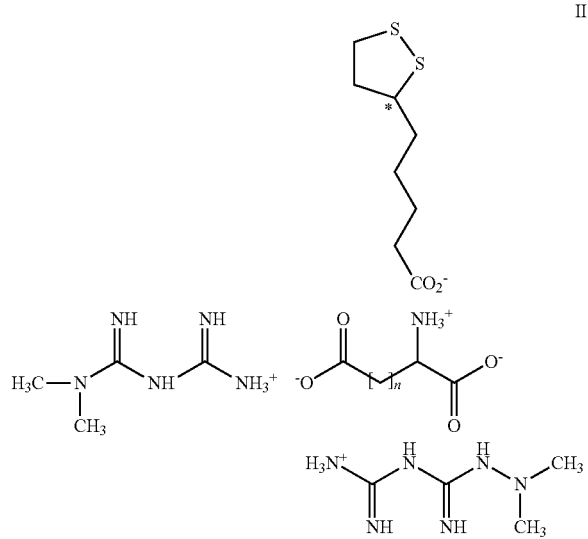

wherein n=1 to 6, and the stereo chemical center depicted by a * is RS (racemate), predominantly R (+), and predominantly S (−) or a pharmaceutically acceptable solvate or hydrate thereof.

2. The composition of claim 1 wherein n=1 and * is RS (±, racemate).

3. The composition of claim 1 wherein n=1 and * is predominantly R(+).

4. The composition of claim 1 wherein n=2 and * is RS.

5. The composition of claim 1 wherein n=2 and * is predominantly R(+).

6. A pharmaceutical composition comprising an amount of the compound of claim 2 effective to treat diabetes, a prediabetic condition, or a diabetic complication and a pharmaceutically acceptable carrier, vehicle, or diluent.

7. A pharmaceutical composition comprising an amount of the compound of claim 3 effective to treat diabetes, a prediabetic condition, or a diabetic complication and a pharmaceutically acceptable carrier, vehicle, or diluent.

8. A pharmaceutical composition comprising an amount of the compound of claim 4 effective to treat diabetes, a prediabetic condition, or a diabetic complication and a pharmaceutically acceptable carrier, vehicle, or diluent.

9. A pharmaceutical composition comprising an amount of the compound of claim 5 effective to treat diabetes, a prediabetic condition, or a diabetic complication and a pharmaceutically acceptable carrier, vehicle, or diluent.

10. A method for treating diabetes in a mammal having diabetes, comprising administering thereto a therapeutically effective amount of the compound of claim 1 in a pharmaceutically acceptable vehicle.

11. A method for treating diabetes in a mammal having diabetes comprising administering thereto a therapeutically effective amount of the composition of claim 2 in a pharmaceutically acceptable vehicle.

12. A method for treating diabetes in a mammal having diabetes comprising administering thereto a therapeutically effective amount of the composition of claim 3 in a pharmaceutically acceptable vehicle.

13. A method for treating diabetes in a mammal having diabetes comprising administering thereto a therapeutically effective amount of the composition of claim 4 in a pharmaceutically acceptable vehicle.

14. A method for treating diabetes in a mammal having diabetes comprising administering thereto a therapeutically effective amount of a composition of claim 5 in a pharmaceutically acceptable vehicle.

15. A method of treating diabetic complications in a mammal, comprising administering thereto a therapeutically effective amount of the composition of claim 1 in a pharmaceutically acceptable vehicle.

16. A method of treating diabetic complications in a mammal, comprising administering thereto a therapeutically effective amount of the composition of claim 2 in a pharmaceutically acceptable vehicle.

17. A method of treating diabetic complications in a mammal having such complications, comprising administering thereto a therapeutically effective amount of the composition of claim 3 in a pharmaceutically acceptable vehicle.

18. A method of treating diabetic complications in a mammal having such complications, comprising administering thereto a therapeutically effective amount of the composition of claim 4 in a pharmaceutically acceptable vehicle.

19. A method of treating diabetic complications in a mammal having such complications, comprising administering thereto a therapeutically effective amount of the composition of claim 5 in a pharmaceutically acceptable vehicle.

20. The method according to claim 15, wherein the diabetic complication is nephropathy, neuropathy, retinopathy, cataracts, myocardial ischemia, or cardiomyopathy.

21. A method of treating a prediabetes syndrome in a mammal having a prediabetes syndrome, comprising administering thereto mammal a therapeutically effective amount of the composition of claim 1 in a pharmaceutically acceptable vehicle.

22. A method of treating prediabetes in a mammal affected thereby, comprising administering thereto a therapeutically effective amount of the composition of claim 2 in a pharmaceutically acceptable vehicle.

23. A method of treating obesity in an obese mammal, comprising administering thereto a therapeutically effective amount of the composition of claim 3 in a pharmaceutically acceptable vehicle.

24. A method of treating obesity in an obese mammal, comprising administering thereto a therapeutically effective amount of the composition of claim 4 in a pharmaceutically acceptable vehicle.

25. A method of treating obesity in a mammal, comprising administering to said mammal a therapeutically effective amount of the composition of claim 5.

26. A method for the manufacture of the composition of claim 1 comprising: (a) adding a solution of racemic or R (+) lipoic acid to a solution of aspartic acid or glutamic acid at a temperature between about 0 degrees C and about ambient temperature to obtain a reaction mixture; and (b) adding free base metformin to the reaction mixture of (a) at a temperature of between about 0 degrees C and ambient temperature.

* * * * *